United States Patent [19]
Mellor

[11] 4,016,879
[45] * Apr. 12, 1977

[54] MULTI-MODE CANNULATING APPARATUS

[75] Inventor: Eli K. Mellor, Burbank, Calif.

[73] Assignee: Dynasciences Corporation, Los Angeles, Calif.

[ * ] Notice: The portion of the term of this patent subsequent to Apr. 8, 1992, has been disclaimed.

[22] Filed: Apr. 7, 1975

[21] Appl. No.: 565,436

Related U.S. Application Data

[63] Continuation-in-part of Ser. No. 390,542, Aug. 22, 1973, Pat. No. 3,875,938.

[52] U.S. Cl. .................... 128/214.4; 128/DIG. 16
[51] Int. Cl.² ........................................ A61M 5/00
[58] Field of Search ............. 128/214.4, 221, 347, 128/348, DIG. 16

[56] References Cited
UNITED STATES PATENTS

| | | | |
|---|---|---|---|
| 2,389,355 | 11/1945 | Goland et al. | 128/214.4 |
| 3,399,674 | 9/1968 | Pannier et al. | 128/214.4 |
| 3,463,152 | 8/1969 | Sorenson | 128/214.4 |
| 3,547,119 | 12/1970 | Hall et al. | 128/214.4 |
| 3,599,637 | 8/1971 | Schwartz | 128/214.4 |
| 3,734,095 | 5/1973 | Santomieri | 128/214.4 |
| 3,756,234 | 9/1973 | Kopp | 128/214.4 |
| 3,757,771 | 9/1973 | Ruegg et al. | 128/214.4 |
| 3,766,916 | 10/1973 | Moorehead et al. | 128/214.4 |
| 3,782,381 | 1/1974 | Winnie | 128/214.4 |
| 3,811,440 | 5/1974 | Moorehead et al. | 128/214.4 |
| 3,853,127 | 12/1974 | Spademan | 128/214.4 |
| 3,875,938 | 4/1975 | Mellor | 128/214.4 |

FOREIGN PATENTS OR APPLICATIONS 2,004,771   11/1969   France ............. 128/214.4

*Primary Examiner*—Dalton L. Truluck
*Attorney, Agent, or Firm*—Donald E. Nist

[57] ABSTRACT

Multiple mode cannulating apparatus is provided wherein in a versatile Y-shaped needle assembly an elastomer plug cooperates with stub tubings to define a Y-shaped port and passage junction of improved design; also, a blood cavity is provided in a carrier removably attached to the apparatus rearwardly of the plug, a cavity image enlarging means is employed; laminar flow junctions are provided at the stub tubings; and the apparatus may be used in both single and two needle dialysis modes.

2 Claims, 22 Drawing Figures

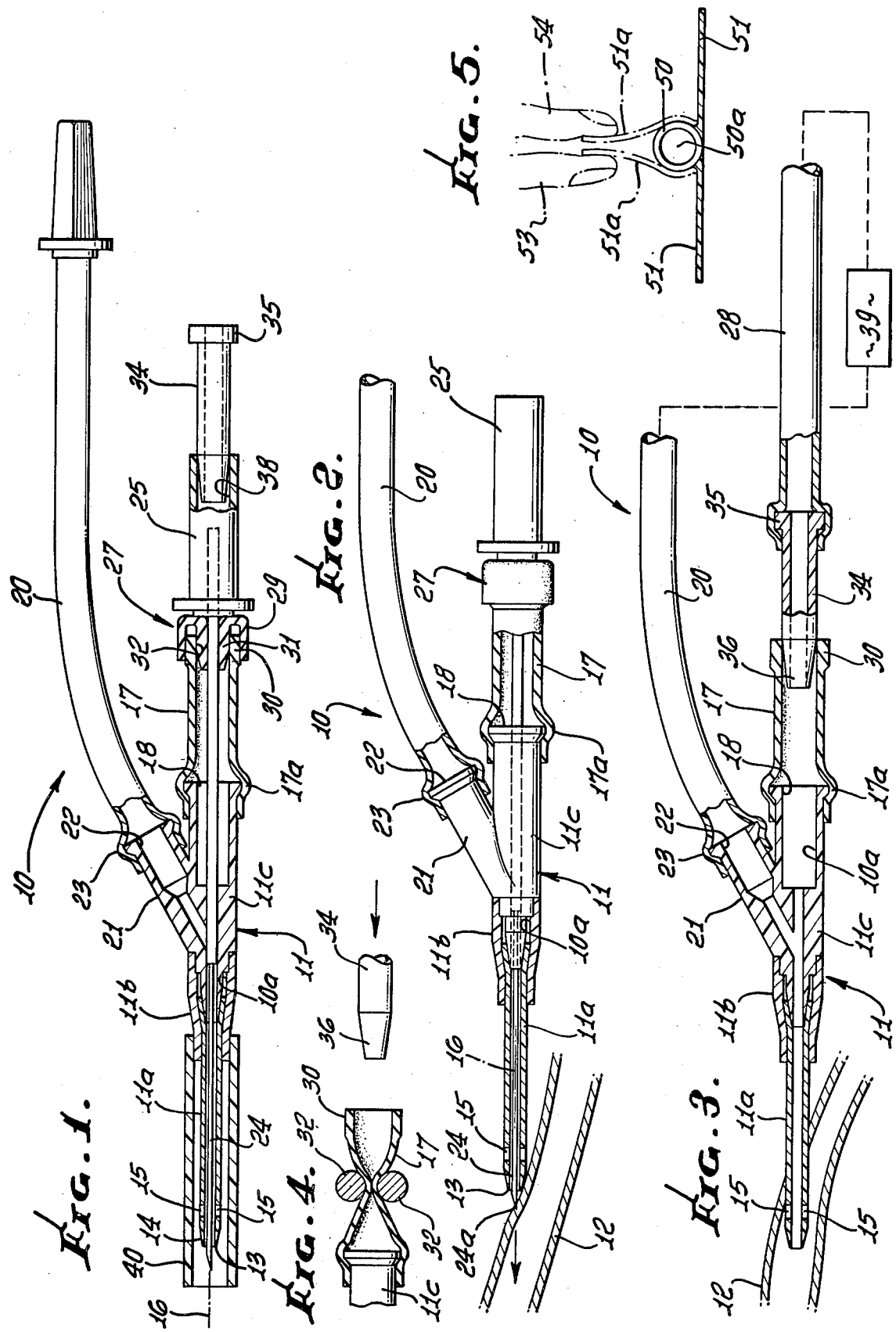

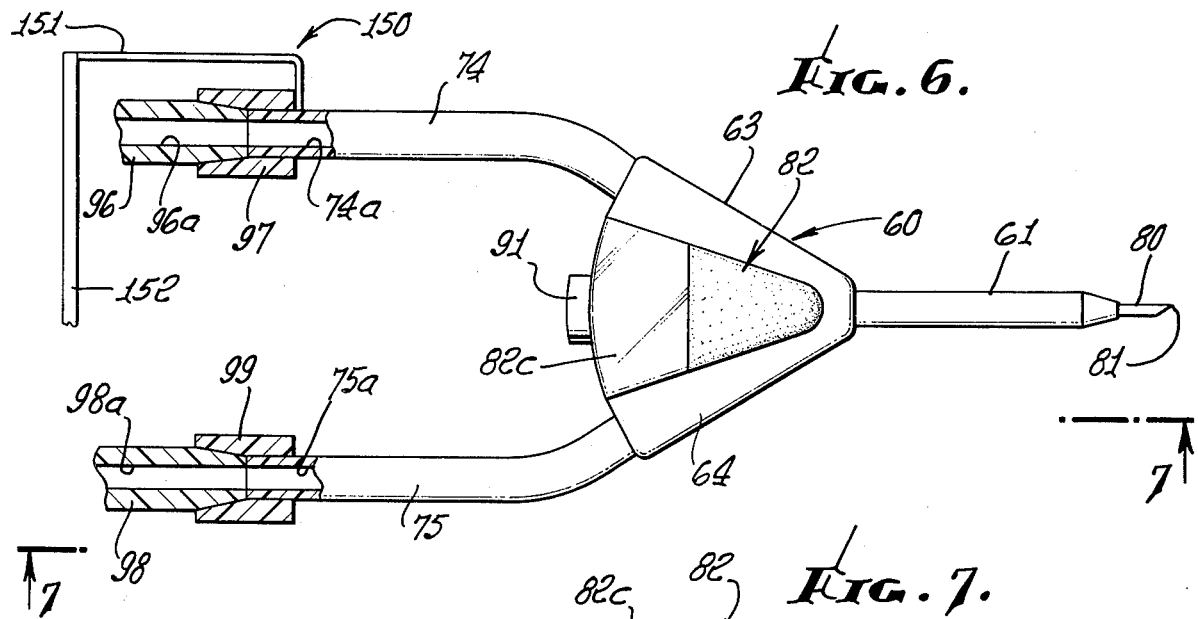
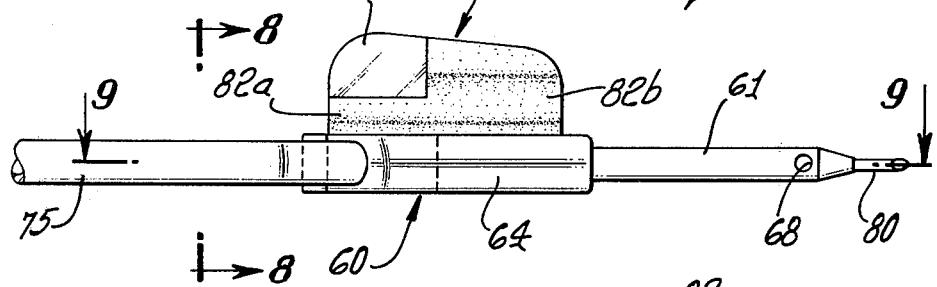
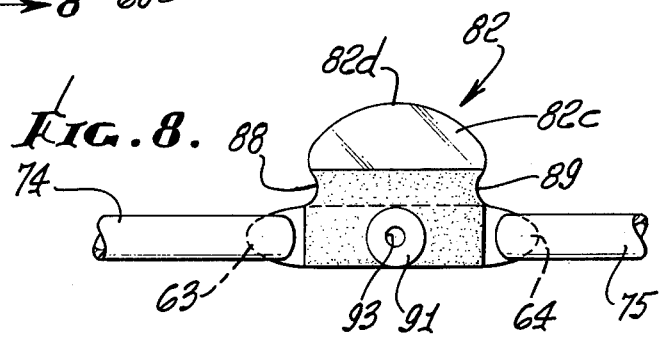
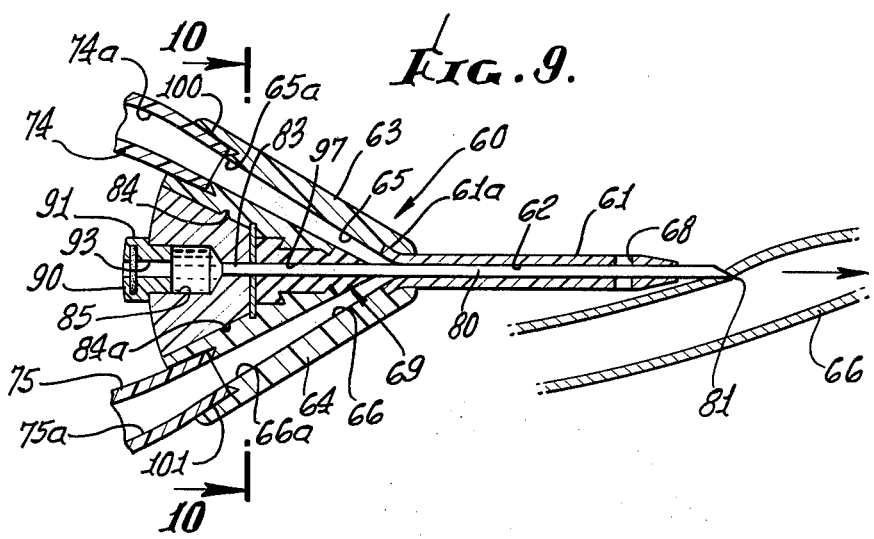

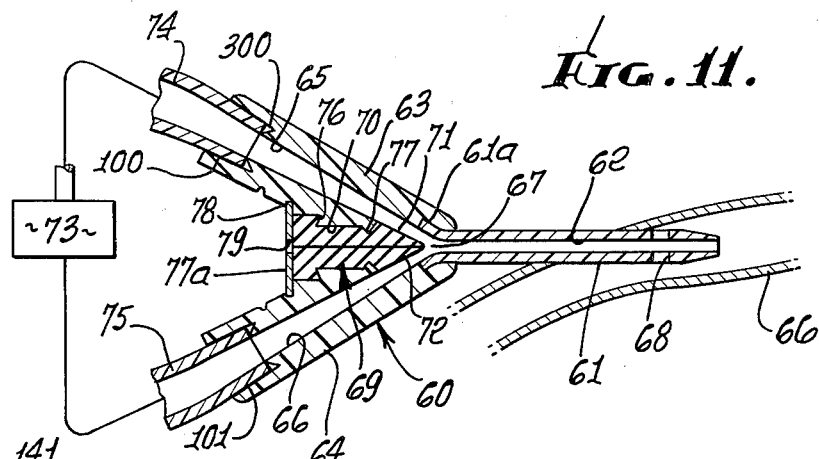
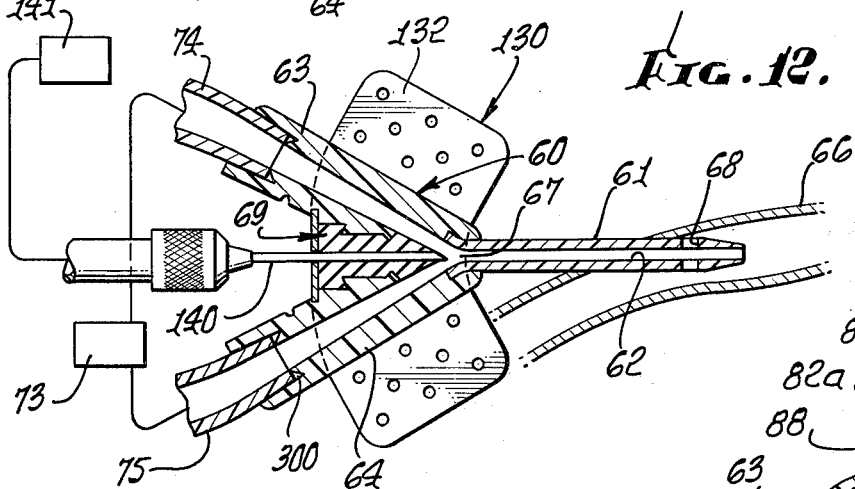
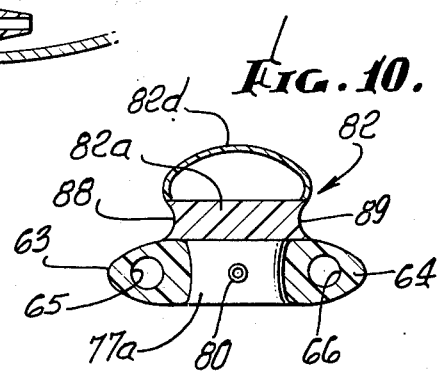
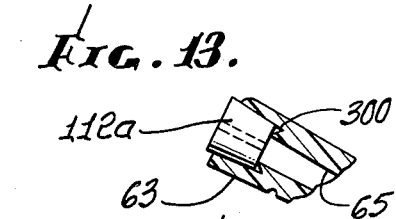
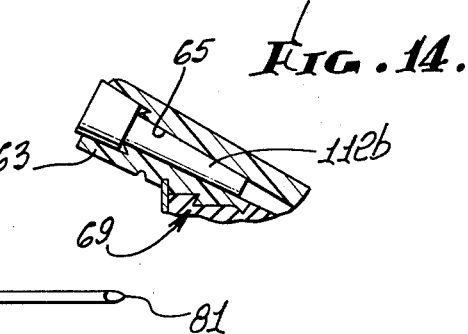
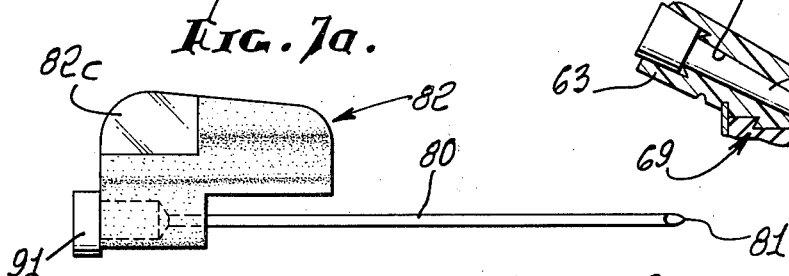
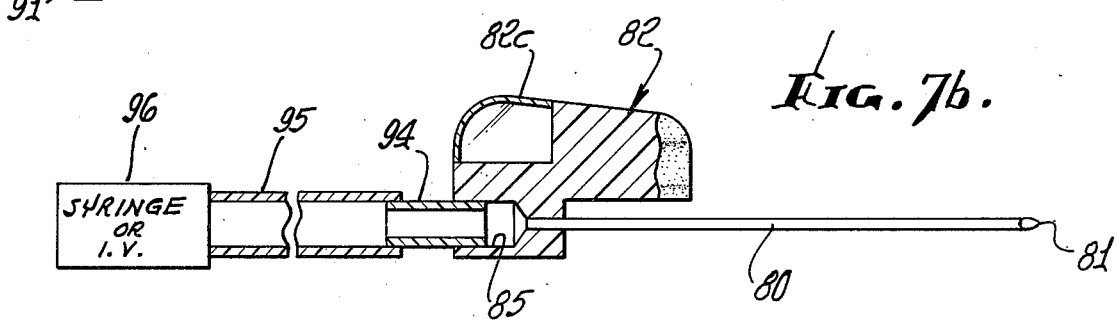

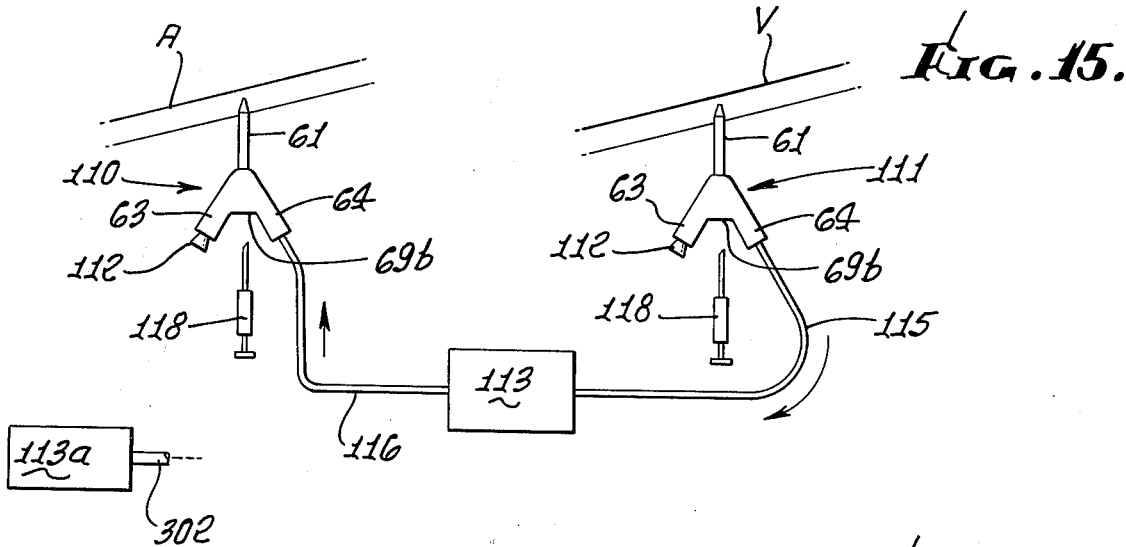
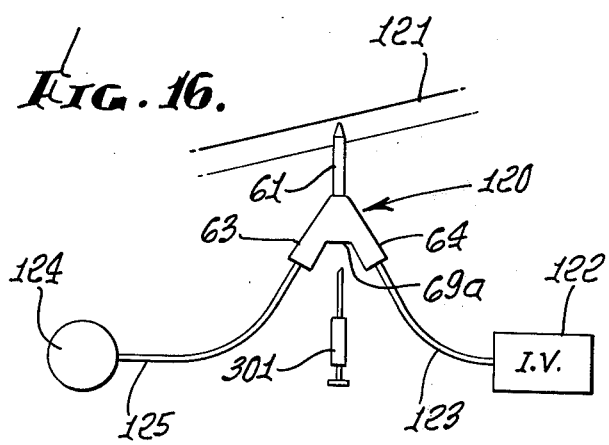
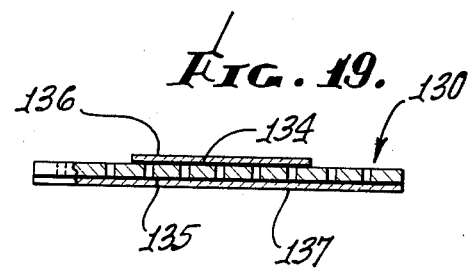
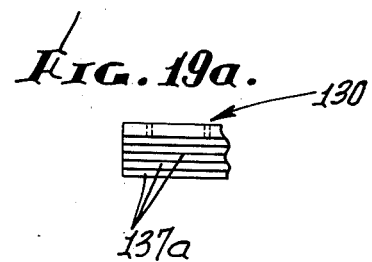
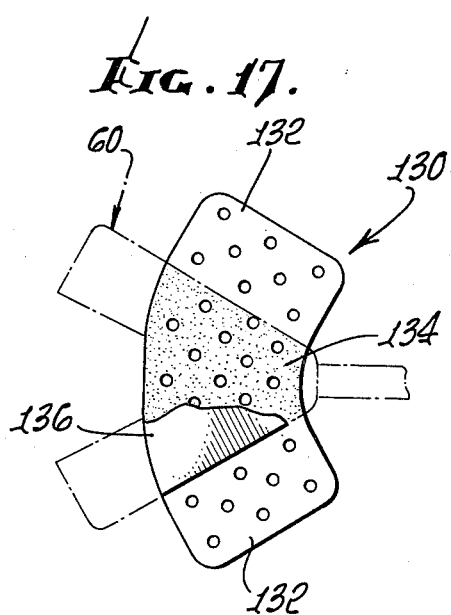
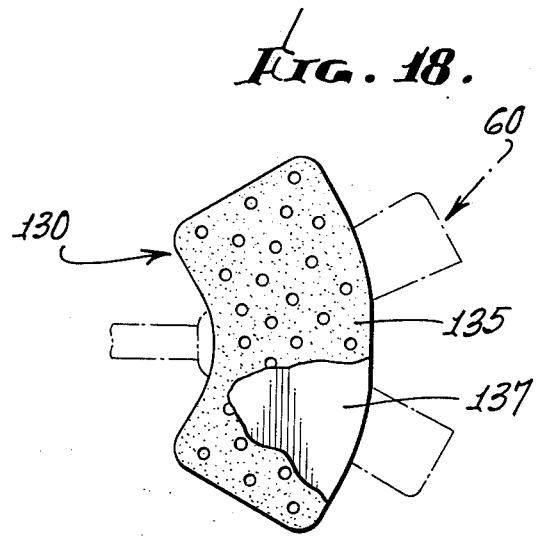

MULTI-MODE CANNULATING APPARATUS

This application is a continuation-in-part of pending application Ser. No. 390,542, filed Aug. 22, 1973, now U.S. Pat. No. 3,875,938.

BACKGROUND OF THE INVENTION

This invention relates generally to apparatus for use with extra-corporeal blood passing equipment, and more particularly concerns the control of blood flow in both withdrawal and return directions between a single blood vessel cannula and the equipment. The present invention employs a novel method and design to substantially reduce dead space volume in the hub of the needle. It also includes other features enabling improved usage as a needle for single needle dialysis, two needle dialysis, monitoring pressure, intravenous administration, drug injection and blood sampling.

The phenomenon termed "recirculation", as used in and associated with single needle hemodialysis, is caused by two contributing factors, i.e. (a) the amount of dialysed blood which is withdrawn from the blood vessel back into the extracorporeal withdrawal circuit, without fully being mixed with the patient's undialysed (uncleansed) blood, and (b) the amount of dialysed blood which is withdrawn out of the needle hub back into the extra-corporeal (withdrawal) circuit.

The first factor is relative and is mostly determined by the pressure gradient (difference) between the pressure in the extra-corporeal blood circuit and the blood vessel pressure. The latter is constant or remains constant as it is determined by the dead space volume of the blood remaining in the hub of the needle, i.e. the greater the dead space and ease of shunting of blood from the infusion side to the withdrawal side, the greater the recirculation and the less efficient the treatment. Conversely, the smaller the dead space and the less tendency for shunting of blood, the less blood recirculated and the more efficient the treatment.

Recirculation in single needle hemodialysis remains as the key disadvantage to continued widespread use of the therapy. Prior art systems and needles have not been able to further reduce this percentage amount of recirculation of blood in order to cause the efficiency of treatment of single needle hemodialysis to be close to that of two needle dialysis. It is true, as previously acknowledged by others skilled in the art that the ability to maximize the stroke volume, i.e. the amount of blood pumped in each alternating cycle, reduces the amount of blood recirculated by decreasing the percentage difference; however, it does not eliminate recirculation by itself.

There is need for rapidly installable and efficiently operable apparatus for controlling the flow of blood between a patient's vessel or vessels and extra-corporeal means such as dialysis equipment. In this regard, it is highly desirable that cannulation and dialysis be carried out with minimum disturbance to the patient, and with equipment that enables efficient and optimized control and monitoring of vessel penetration, blood flow and infusion of other solutions. Prior apparatus of which I am aware does not incorporate the unusually advantageous features of construction, modes of operation and surprisingly favorable results afforded by the invention, as will appear.

SUMMARY OF THE INVENTION

The invention concerns multiple mode, cannulating apparatus wherein a blood vessel puncturing rod or needle is removable from a tubular body having a forward stem penetrating the vessel, and wherein the body has a rearward extension allowing pinch-off between the time that the rod is removed and auxiliary tubing is coupled to the extension. Accordingly, blood may then be circulated from and to the body via that tubing and auxiliary tubing connected with a body side port, as will be seen. This assures that during such blood flow treatment, the puncture rod is removed from the body so as not to inadvertently re-puncture the vessel if the equipment is caused to be moved on or relative to the patient.

Other objects include the provision of a removable elastomer plug on the insert, which seals off between the insert and puncture rod; the provision of an adapter duct to couple the auxiliary tubing to the flexible extension; and the provision of tabs or wings on the body to facilitate its use and connection to the skin of a patient, as will be seen.

Additional important objects include the provision of a versatile Y-shaped needle assembly; the minimizing of "dead space" at the Y-shaped junction between two side ports and a main passage in the needle body; the minimizing of the length of the total structure projecting forwardly of that junction and the maximizing of the length of the cannula penetrating the vessel; the provision of an elastomer plug retained by the body to extend to that junction and form portions of side port walls at the tip of the plug; the provision of an easily manually graspable carrier for the vessel puncturing needle or stylette that penetrates the plug and extends in the passage, the carrier removably attached to the body; the provision of a blood receiving cavity in the stylette carrier and which is visible through a window, the latter preferably providing cavity image magnification; the provision of port and tubing bore walls which are flush and enable laminar flow of blood and other liquid; the provision of means to easily attach the needle body to a patient's skin; and both single and two needle dialysis set-ups employing the same basic needle design.

These and other objects and advantages of the invention, as well as the details of illustrative embodiments, will be more fully understood from the following description and drawings, in which:

DRAWING DESCIPTION

FIG. 1 is an enlarged vertical section taken through a multiple mode needle embodying the invention;

FIG. 2 is a view like FIG. 1 showing one mode of needle operation;

FIG. 3 is a view like FIG. 1 showing another mode of needle operation;

FIG. 4 is a fragmentary view showing a pinch-off configuration;

FIG. 5 is a view in vertical section through a body of the type shown in FIG. 1;

FIG. 6 is a plan view showing a modified multiple mode needle assembly;

FIG. 7 is a side elevation of the FIG. 6 needle assembly;

FIG. 7a is a side elevation showing a removed stylette and handle-housing supporting a plug;

FIG. 7b is a view like FIG. 7a showing a mode of use of the removed stylette and handle-housing;

FIG. 8 is a vertical end elevation on lines 8—8 of FIG. 7;

FIG. 9 is a plan view in section showing one mode of use of the FIG. 6 assembly;

FIG. 10 is a vertical elevation taken in section on lines 10—10 of FIG. 9;

FIG. 11 is a plan view in section showing another mode of use of the FIG. 6 assembly;

FIG. 12 is a plan view in section showing still another mode of use of the FIG. 6 assembly;

FIGS. 13 and 14 are fragmentary sections showing plugs in stub tubings;

FIG. 15 is a schematic showing of dialysis employing two needles as described;

FIG. 16 is a schematic showing of another use of the single needle as described;

FIG. 17 is a top view of needle holder;

FIG. 18 is a bottom view of the FIG. 17 needle holder;

FIG. 19 is an end view of the FIG. 17 needle holder; and

FIG. 19a is a fragmentary view of a modified needle holder.

DETAILED DESCRIPTION

The cannulating needle apparatus 10 of FIG. 1 includes an axially extending tubular body 11 defining a blood flow passage 10a. The body includes telescopically interfitting and bonded plastic portions 11a, 11b and 11c, portion 11a comprising a forward flexible stem or cannula insertible into a blood vessel seen at 12 in FIGS. 2 and 3. Portions 11b and 11c are typically relatively inflexible.

Stem portion 11a contains porting to pass blood flow to and from the vessel as illustrated for example by a terminal port 13 at the stem forwardly tapered end 14, and lateral side ports 15 in rearwardly closely spaced relation to port 13. Four such ports 15 may be provided at about 90° intervals about axis 16, whereby at least one or more ports will remain in the blood providing open communication with the vessel interior, despite possible blocking of another port or ports by the vessel wall.

A rearward tubular extension 17 is provided on the body to extend axially rearwardly from a body rear port 18. Extension 17 may consist of laterally flexible plastic tubing, allowing pinch-off as shown in FIG. 4, and for purposes as will appear. Typically, the forward portion 17a of the extension is telescopically fitted over the rearward extent of the body portion 11c, as shown.

The body portion 11c also has one side port for conducting blood flowing between passage 10a and first auxiliary tubing such as is indicated at 20. For such purpose, that body portion 11c has a rearwardly and sidewardly angled stub duct 21 defining a side port 22, the tubing 20 telescopically fitted over the stub duct at 23.

In order to insert the stem 11a into the blood vessel 12, it is first necessary to puncture same. For this purpose a rearwardly removable rod 24 is provided to extend axially within the passage 10a and to have a sharp tip 24a. The portion 11a may be flexible, or inflexible. An enlargement 25 functioning as a handle is attached to the rear end of the rod and exposed rearwardly of extension 17, so as to be manually rearwardly retracted. A sealing elastomer plug 27 serves to transmit force from the pusher 25 to the extension 17.

The plug 27 comprises one form of means for sealing off between the rod and extension 17. Further, it is constructed so as to be manually removable off the extension when the rod is rearwardly removed from the body, in order to accommodate subsequent coupling of other auxiliary flexible, blood flow tubing 28 with extension 17, as for example is illustrated in FIG. 3. For this purpose, the plug 27 may have an annular lip 29 fitting telescopically over the extension end 30, and an insert 31 fitting into the extension bore 32. The insert 31 has a tight, sliding and sealing fit with rod 24, to prevent leakage of blood rearwardly from extension 17, when the vessel is punctured.

Subsequent to such puncturing, the rod 24 is retracted rearwardly. During or immediately following such removal, the extension is clamped to pinch-off, as seen in FIG. 4, clamp elements 32 representing manual or mechanical clamping means. Also the plug 27 is then removed. This makes possible the operative attachment of tubing 28 to the extension rear end portion 30, without undue leakage of blood. In this regard, such attachment is facilitated by use of an adapter duct or part 34 having a flanged rear end 35 to which tubing 28 may be attached. Such attachment may be carried out prior to insertion of the tapered forward end 36 of the duct 34 into the bore 32 of the extension 17, to have a tight sealing fit therewith. FIG. 4 shows the approach of the duct end 36 toward the rear end 30 of the extension, for simultaneous insertion of the duct end and release of the clamp elements 32. The adapter duct 34 may initially be removably carried by the pusher 25, as by penetration of the tapered end 36 into tight fitting relation with bore 38 to provide antiseptic protection for end 36.

The numeral 39 in FIG. 3 indicates the provision of extra corporeal means connected with auxiliary tubing 20 and 28 for circulating blood to and from the vessel 12 via the passage 10a. Such means may for example comprise dialysis equipment as described in my co-pending U.S. patent application Ser. No. 244,399, filed Apr. 17, 1972, now abandoned. Numeral 40 in FIG. 1 indicates a protective length of tubing initially fitting on the body 11, and about stem 11a.

FIG. 5 is a vertical section through a body 50 of the type seen in FIG. 1, the axis indicated at 50a. Plastic tabs or wings 51 are integrally formed with the body to be placed upon the skin of a patient at the time cannulation is to commence. The wings are then elevated as shown by the broken lines 51a, and retained between the technician's thumb and first finger 53 and 54, to provide a grip on the apparatus allowing it to be advanced with the rod or needle tip 24a extended, to achieve cannulation. Thereafter, the wings 51 are allowed to drop back to the full line positions shown, for suitable attachment to the patient's skin, holding the equipment in place during blood treatment.

Referring now to FIGS. 6–12, an axially extending tubular body 60 includes a forward stem portion 61 insertible into a blood vessel 66, as more particularly seen in FIG. 11. The body contains a forwardly extending liquid flow passage 62 and at least one side port for conducting liquid (as for example blood, intravenous fluid, etc.) between auxiliary tubing and the passage 62. For example, the body may have forwardly tapering stub tubes 63 and 64 defining side ports 65 and 66 intersecting with passage 62 at junction 67. Passage 62 is relatively close to the forward end of stem 61 by virtue of the body construction. Note in this regard the reception of the annularly rearwardly flaring extent 61a of the stem in the common nose of the stub tubing. The latter may consist of relatively rigid molded plastic material, whereas stem 61 consists preferably of somewhat flexible plastic material or metal. Also, the stem may contain side ports 68 proximate its forward end to further accommodate blood flow between the passage 62 and the interior of the vessel 66.

An elastomer sealing plug 69 is carried by the body and received forwardly in a body rear port 70 in alignment with the forward axis of stem 61. Plug 69 tapers forwardly toward junctions 67 to define forwardly tapering inner walls 71 and 72 of the ports 65 and 66. The construction is such that the side ports are seen to taper forwardly, i.e. narrow, as they approach the junction 67 whereby the "dead space" at the junction is minimized, so that shunting or reverse circulation of fluid between the ports is also minimized during use such as single needle dialysis. Accordingly, the overall size of the equipment may be reduced with greater patient acceptance and ease of handling; in addition the equipment is more efficient in operation.

FIG. 11 illustrates such use, whereby blood is first withdrawn from the vessel 66 to flow via passage 62, port 65 and tubing 74 to the dialysis equipment 73, during one time or pressure interval; and treated blood is returned from equipment 73 via tubing 75, port 66 and passage 62 to the vessel 66 during another time or pressure interval, this process being cyclically repeated. An annular recess 300 formed in each stub duct is adapted to receive excess adhesive when the terminal of tubing 74 is bonded to the stub duct.

Note that there are typically multiple annular interfitting plug and body shoulders as at locations 76 and 77, locking the plug to the body and sealing off therebetween. For example annular interfitting shoulders at 76 block forward displacement of the plug in the body rear bore 70, and annular interfitting shoulders at 77 block rearward displacement of the plug in bore 70. Also, a rigid shield 77a is located at the rear end of the plug and connected with the body at locations 78, the shield aiding in holding the plug in place. The shield contains an axial through bore at 79 to pass a hollow needle or stylette seen at 80 in FIG. 9.

FIG. 12 shows the use of an auxiliary needle 140 penetrating the plug 69 and terminating at junction 67 to allow administration of fluid to the patient during dialysis, and a source of such fluid appears at 141. The latter may also represent a pressure monitor or related sensing equipment.

As seen in FIGS. 6-10, rearwardly removable structure extends axially within passage 62 and through plug 69. That structure may be considered to include the tubular needle 80 which has a blood vessel puncturing forward tip 81 illustrated in FIG. 9. Also, such structure includes a carrier 82 for the needle, to which the latter is attached at 83. The carrier is generally delta-shaped and is removably attached to the inner walls of stub tubes 63 and 64 as at interlocking locations 84 and 84a. The latter enable "snap" attachment of the carrier to the stub tubes, and pull-off detachment of the carrier from the latter, as desired. The carrier may consist of plastic material, and it contains a blood receiving cavity 85 located rearwardly of the plug and communicating with needle 80 to quickly receive blood when the vessel 66 is punctured. The structure, such as carrier 82, projects upwardly above the cavity, and forwardly over the plug, as seen in FIG. 7 as locations 82a and 82b, to define lateral concave sides 88 and 89 adapted to be easily grasped, manually, for forwardly attaching and rearwardly detaching the carrier to and from the body 60, as described. Also, the structure is translucent at 82c for defining a window to permit viewing of blood reception in the cavity, indicating that the vessel has been punctured. The window structure 82c may have an upwardly facing, convex lens surface 82d by which an enlarged upwardly projecting image of the blood in the cavity is formed, for viewing.

Referring now to FIGS. 7a and 9, a filter 90, such as a porous filter, is shown as carried by tubular plug 91 removably inserted into the rear end of cavity 85. The filter passes air outwardly from cavity 85, via a port 93 in the plug, but blocks outward flow of blood from the cavity, allowing rapid in-flow of blood to the latter.

In FIG. 7b, the carrier 82 and needle 80 are shown. In that illustration, a male tubular adapter 94 is fitted into the bore of cavity 85, there being flexible or other tubing 95 attached to the adapter. A means 96 such as a syringe is connected with the tubing and is operable to inject liquid (saline solution or other) through the adapter, cavity and needle 80 to prime the needle. Such priming may take place with the assembly connected to the body 60, as by removable attachment of body 82 thereto in the manner shown in FIG. 9, with needle 80 penetrating stem 61. The needle tip 81 may then be caused to puncture vessel 66, and the syringe plunger slightly withdrawn to obtain a small amount of blood in the adapter tubing and syringe. Once this is done, the needle 61 is secured to the patient, as by taping etc., and the blood and drug or other treatment solution in the syringe are infused by the syringe into the vessel via needle 80. Next, the carrier handle walls 88 and 89 are grasped and pulled rearwardly to detach the carrier from the body 60 and to withdraw stylette needle 80 from the stem 61 and rearwardly through the plug 69, the latter sealing off the passage 97 therethrough. The catheter stem 61 remains penetrating the vessel 66 and dialysis may be carried out as previously described, or other functions may be performed.

FIG. 9 shows the bore 74a of tubing 74 to be flush, or diametrically equal, to the bore 65a of port 65; likewise, the bore 75a of tubing 75 is flush with the bore 66a of port 66. These elements may be bonded together at locations 100 and 101. Accordingly, optimum laminar flow patterns are achieved, without creation of flow turbulence at the joints. FIG. 6 shows a similar arrangement with end to end tubular members 74 and 96 having flush bores 74a and 96a, an adapter 97 connecting the members and bridging the joint therebetween. Likewise end to end members 75 and 98 have flush bores 75a and 98a with an adapter 99 bridging the joint and connecting these members. The members may be adhesively bonded to the adapters.

The needle as described above may be employed in either single needle dialysis (see FIG. 11) or so-called two-needle dialysis. The latter is shown in FIG. 15 wherein the stem 61 of needle unit 110 penetrates an artery A, and the stem 61 of like needle unit 111 penetrates a vein V. Stub ducts 63 are blocked as by plugs 112, whereas the stub ducts 64 respectively have connection with the input and output sides of dialysis equipment 113, as via tubing 115 and 116. Monitoring or other equipment 113a (such as I.V. means) may be connected with the blocked stub ducts after removal of the plugs 112, if desired; also, syringes 118 or other means (such as I.V. apparatus) may be connected with the needle units via penetration of the elastomer plugs 69 previously described. Typical plugs 112 are shown in FIGS. 13 and 14, the former being a short plug 112*a* and the latter a long tapered plug 112*b* to fill port 65. FIG. 16 shows a single needle unit 120 having a stem 61 penetrating a vessel 121. Intravenous liquid supply means 122 is connected with stub duct 64 via tubing 123, and a device 124 is connected with stub duct 63 via tubing 125. Device 124 may comprise a pressure monitor, sampling syringe, etc.

FIGS. 17–19 illustrate the provision of an adhesive member 130 connected or connectible with the underside of the needle body 60, in the manner as for example is shown in FIG. 12. The adhesive member includes a mid-portion 131 connectible with the body, and end flaps 132 which are flexible, and may be pressed down on the skin surface to adhere thereto. Note the forwardly angled configuration of the flaps to resist rearward retraction of the body preventing withdrawal of stem or cannula from a penetrated vessel. The member 130 may consist of a sheet of fabric, plastic etc., which is perforated to permit "breathing" of the skin therethrough. FIG. 19 illustrates top and bottom adhesive layers 134 and 135 on the flap material, the layer 134 adapted to adhere to the needle body, and the layer 135 adapted to adhere to the skin. Removable protective paper or other layers 136 and 137 cover the adhesive. The modified holder seen in FIG. 19*a* includes the fabric 130 as in FIG. 19; however, multiple removable paper or other layers 137*a* and adhesive thereon are stacked under fabric 130 to support the needle body in elevated condition relative to the patient's skin. Layers 147*a* may be selectively peeled off to vary the supported "height" of the needle body.

Finally, FIG. 6 also shows a holder 150 including a rigid bracket 151 attached to the projecting from and parallel to tubular adapter 97, and an adhesive strip 152 attached to the bracket. Strip 152 may be clipped or wrapped about the connecting tubing to prevent detachment of the apparatus.

Referring again to FIG. 16, element 124 may alternatively represent a source of medication or drugs administered to the patient via tubing 125 single needle 120 at the same time that I.V. solution is being administered. In addition, a syringe 301 may be inserted into the needle at plug site 69*a*, for administering fluid to the patient. Either of elements 124 and 301 may be employed for blood sampling.

Referring again to FIG. 15, an element 113*a* may be connected via tubing 302 with either of the stub tubings 63 of the two needles 110 and 111, after removal of plugs 112, for pressure monitoring, administering other solution, or removing or sampling blood in the needle. Syringes 69 may be applied to plug sites 69*b* to penetrate the plugs for administering solution or withdrawing blood.

I claim:

1. In cannulating apparatus, the combination comprising:
    a. an axially extending tubular body defining a blood flow passage and having a forward stem portion insertible into a blood vessel, said body defining two side ports and including two stub ducts defining forwardly tapering bores communicating at their forward ends with said side ports for conducting blood flowing between said passage and auxiliary tubing connectible at rearward ends of said ducts, said body also defining a rear port in alignment with said axis,
    b. an elastomer plug carried by said body in alignment with said rear port and projecting to the junction of said side ports and said flow passage, said plug defining forwardly tapering inner wall portions of said side ports,
    c. rearwardly removable structure extending axially within said passage and axially through said plug, said structure having a vessel puncturing forward tip, and
    d. said side ports intersecting said passage at a location relatively close to the forward end of said stem portion.

2. The apparatus of claim 1 including tubing connected with at least one said stub duct, said tubing and stub duct having bores which are equal at the junction therebetween.

* * * * *